US010945442B2

(12) United States Patent
Vilà Rifà et al.

(10) Patent No.: US 10,945,442 B2
(45) Date of Patent: Mar. 16, 2021

(54) MITE COMPOSITION, METHOD FOR REARING A PHYTOSEIID PREDATORY MITE SPECIES, AND USE OF THE COMPOSITION FOR CONTROLLING CROP PESTS

(71) Applicant: AGROBIO S.L., Almeria (ES)

(72) Inventors: Enrique Vilà Rifà, Almeria (ES); Don Griffiths, Middlesex (GB)

(73) Assignee: AGROBÍO S.L., Almeria (ES)

( * ) Notice: Subject to any disclaimer, the term of this patent is extended or adjusted under 35 U.S.C. 154(b) by 357 days.

(21) Appl. No.: 15/858,081

(22) Filed: Dec. 29, 2017

(65) Prior Publication Data

US 2018/0160688 A1 Jun. 14, 2018

Related U.S. Application Data

(62) Division of application No. 13/642,665, filed as application No. PCT/EP2011/056504 on Apr. 22, 2011, now abandoned.

(30) Foreign Application Priority Data

Apr. 23, 2010 (EP) .................................... 10160898

(51) Int. Cl.
*A01N 63/10* (2020.01)
*A01K 67/033* (2006.01)
*A01N 63/00* (2020.01)
*A23K 50/90* (2016.01)

(52) U.S. Cl.
CPC ............ *A01N 63/10* (2020.01); *A01K 67/033* (2013.01); *A01N 63/00* (2013.01); *A23K 50/90* (2016.05)

(58) Field of Classification Search
None
See application file for complete search history.

(56) References Cited

U.S. PATENT DOCUMENTS

2013/0202714 A1 8/2013 Rifa et al.

FOREIGN PATENT DOCUMENTS

| WO | WO 2007/075081 | 7/2007 |
| WO | WO 2008/015393 | 2/2008 |
| WO | WO 2008/104807 | 9/2008 |

OTHER PUBLICATIONS

De Albuquerque (Neotropical Entomology (2008), vol. 37, No. 3, pp. 328-333—English translation provided).*
Escudero "Life-history of predatory mites Neoseiulus californicus and Phytoseiulus persimilis (Acari: Phytoseiidae) on four spider mite species as prey, with special reference to Tetranychus evansi (Acari: Tetranychidae)," Biological Control, Mar. 2005, vol. 32, No. 3, pp. 378-384 (Abstract only).
Official Action for Canada Patent Application No. 2,796,953, dated Mar. 14, 2018, 1st page only.
Escudero "Life-history of predatory mites Neoseiulus californicus and Phytoseiulus persimilis (Acari: Phytoseiidae) on four spider mite species as prey, with special reference to Tetranychus evansi (Acari: Tetranychidae)," Biological Control, Mar. 2005, vol. 32, No. 3, pp. 378-384.
McMurtry et al. "Revision of the lifestyles of phytoseiid mites (Acari: Phytoseiidae) and implications for biological control strategies," Systematic & Applied Acarology, 2013, vol. 18, No. 4, pp. 297-320.
Official Action for Canada Patent Application No. 2,796,953, dated Mar. 28, 2019, 5 pages.
Afifi et al. "Comparative Attractancy of Three Phytoseiid Predator Species to the Twospotted Spider Mite *Tetranychus urticae* Koch," Transactions of the Kentucky Academy of Science, 1988, vol. 49, No. 3-4, pp. 120-127.
Cunnington "Resistance of the Grain Mite *Acarus siro* L. (Acarina, Acaridae) to Unfavourable Physical Conditions Beyond the Limits of Its Development," Agriculture, Ecosystems and Environment, Nov. 1984, vol. 11, No. 4, pp. 319-339.
Database Biosis [Online] Biosciences Information Service, Philadelphia, PA, US; 1988, Afifi A M et al. "Comparative Attractancy of 3 Phytoseiid Predator Species to the Two-spotted Spider Mite Tetranychus-Urticae Koch," XP882588368, Database Accession No. PREV198987046608 abstract & transactions of the Kentucky Academy of Science, vol. 49, No. 3-4, 1988, pp. 128-127, ISSN: 8823-8881.
Grasswitz "Chemical Ecology and Pest Management," Encyclopedia of Life Support Systems (EOLSS), UNESCO, 2003, 2 pages.
Griffiths "Chapter 15: Biological Control of Mites," Integrated Pest and Disease Management in Greenhouse Crops, Ed. Albajes et al., Dordrecht, Netherlands, Kluwer Academic Publishers, 1999, pp. 217-234.
Hughes "The Mites of Stored Food and Houses," Ministry of Agriculture, Fisheries and Food, Technical Bulletin 9, London, Her Majesty's Stationery Office, 1976, pp. 1-7.
McMurtry et al. "Life-styles of Phytoseiid mites and their roles in biological control." Annual Review of Entomology, Jan. 1997, vol. 42, pp. 291-321 (Abstract only).
Nielsen Per Sejero: "Developmental time of Blattisocius tarsalis (Acari: Ascidae) at different temperatures", Experimental and Applied Acarology, vol. 25, No. 7, 2801, pp. 605-688, XP882588369, ISSN: 8168-8162 the whole document, 2001.

(Continued)

*Primary Examiner* — Susan Hoffman
(74) *Attorney, Agent, or Firm* — Sheridan Ross P.C.

(57) ABSTRACT

The present invention relates to a mite composition, the rearing thereof and to the use of the composition for controlling crop pests. The invention provides a mite composition comprising: —a rearing population of a phytoseiid predatory mite species, —a population of at least one species from the order Astigmata, and—optionally a carrier, wherein the population of the species from the order Astigmata is not alive. In particular the population of the species from the order Astigmata is in fast frozen fom1. The composition is used for controlling crop pests, such as thrip species. The crops may be greenhouse grown crops and open field crops.

14 Claims, No Drawings

(56) References Cited

OTHER PUBLICATIONS

Ramakers et al., "Start of commercial production and introduction of Amblyseius mckenziei Sch. & Pr. (Acarina: Phytoseiidae) for the control of Thirps tabaci lind. (Thysanoptera: Thripidae) in glasshouses" Mededelingen Faculteit Landbouwwetenschappen Rijksuniversiteit Gent vol. 47, No. 2, pp. 541-545 (1982).
Stenseth "Cold Hardiness in the Two-Spotted Spider Mite (*Tetranychus urticae* Koch)," Entomologia Experimentalis et Applicata, Mar. 1965, vol. 8, No. 1, pp. 33-38.
Zdarkova et al. "The effects of physical factors on survival of stored food mites," Experimental and Applied Acarology, Mar. 1993, vol. 17, No. 3, pp. 197-204.
Official Action for U.S. Appl. No. 13/642,665, dated Jan. 30, 2015 Restriction Requirement.
Official Action for U.S. Appl. No. 13/642,665, dated Jul. 9, 2015.
Official Action for U.S. Appl. No. 13/642,665, dated Apr. 1, 2016 9 pages.
Official Action for U.S. Appl. No. 13/642,665, dated Mar. 2, 2017 9 pages.
Official Action for U.S. Appl. No. 13/642,665, dated Sep. 29, 2017 7 pages.
Official Action for Canada Patent Application No. 2,796,953, dated Jun. 11, 2020, 3 pages.

\* cited by examiner

MITE COMPOSITION, METHOD FOR REARING A PHYTOSEIID PREDATORY MITE SPECIES, AND USE OF THE COMPOSITION FOR CONTROLLING CROP PESTS

CROSS-REFERENCE TO RELATED APPLICATIONS

This application is a divisional application of U.S. Ser. No. 13/642,665, filed Jan. 2, 2013, now abandoned, which is a 371 of International Application PCT/EP2011/056504, filed Apr. 22, 2011, which claims priority from EP Patent Application No. 10160898.2, filed Apr. 23, 2010, the contents of which are incorporated herein by reference.

This invention relates to a mite composition comprising a rearing population of a phytoseiid predatory mite species, a population of at least one species from the order Astigmata, and optionally a carrier.

Further the invention relates to a method for rearing a phytoseiid predatory mite.

According to a further aspect the invention relates to the use of the mite composition for controlling a crop pest.

Agricultural crops, especially protected crops, are grown intensively over a relatively short growing season. Pests which invade them almost always result from outside invasions and, because the crop provides a very favourable food supply, they can reach high densities very quickly. Thus, any introduction of a predator aimed at controlling them must be inundative. That is, large numbers of predators must be introduced in a regular programme of introductions, sufficient to keep the pest population below the level at which it can cause economic loss.

Therefore, any commercial rearing of a predator, used inundatively, must be able to produce high numbers of the predator throughout the growing season; nowadays under modern glasshouse regimes this means almost year round. To rear a predator requires that it is provided with sufficient suitable prey for rapid population growth, but commercially this needs to be at a realistic cost.

The most successful commercial productions to date are those in which the prey is a species belonging to the mite order of the Astigmata. These are small, soft bodied individuals known collec-tively as 'stored food' or 'stored product' mites, and as such live on a wide range of foodstuffs, especially those of a farinaceous nature, and are commonly found in stores and domestic dwellings (Hughes, 1976). Using the correct food materials and the right physical conditions these astigmatid mites can be reared in-doors in containers to provide high population concentrations at reasonable cost. Currently, all phytoseiid predators being produced commercially are reared on an astigmatid species.

The commercial product usually consists of a neutral substrate which supports the predators in a three dimensional space, plus the astigmatid prey species, together with its farinaceous type food supply.

After certain adjustments aimed at giving a balanced ratio of predator to prey, this same composition forms the basis of the product offered for sale. Accordingly, on application into the crop, it will contain a live population of the astigmatid host.

This current commercial product causes a number of problems. The presence of food material such as bran used to feed the prey during predator production causes problems of fungal contamination. A further problem is the occurrence of prey imbalance, in which too high or too low prey ratios can cause poor predator development. Further, some astigmatid species can cause crop damage by feeding on younger tender plants.

Moreover, some of the astigmatid species cause serious problems in the food industry. For example, on a world wide basis stored dried fruits of all kinds are invariably infested with a major pest namely, the dried fruit mite, *Carpoglyphus lactis*, (Hughes, 1976; Cobagnolu, 2008). Co-incidentally, this is the species which is being used more and more as the preferred host on which to rear phytoseiid predators, of which the predator *Amblyseius swirskii* is such an example.

The present invention solves these problems by providing a mite composition which contains only one live population, namely the predator.

Accordingly, the invention provides a mite composition comprising:
  a rearing population of a phytoseiid predatory mite species,
  a population of at least one species from the order Astigmata, and
  optionally a carrier,
characterised in that the population of the species from the order Astigmata is not alive.

The astigmatid species which will provide the nutrients for the predators will be reared in isolated containers capable of oxygen exchange and of suitable dimensions. They will be reared under physical conditions around 25° C. and a relative humidity (RH) of 75-85%.

Their food materials will vary according to the particular species being reared. The diet will contain compositions of the following ingredients: yeast particles, wheat flour, particles of dried fruit material, a sugar such as dextrose, etc. The food material will be added to a bulking agent such as vermiculite particles, thus providing a three dimensional environment in which the astigmatid species can breed freely.

Astigmatid species can be expected to reach an intrinsic rate of increase varying from about 2.5 to 6 in about seven to nine days (Cunnington, 1965 & 1969). Once such a population has obtained the required density, and the food material is reaching exhaustion, the population will be killed in order to obtain a dead population. In a preferred embodiment of the invention, the composition will be fast frozen, using the technique employed to freeze food for human consumption, namely immersion in an atmosphere of gaseous liquid nitrogen. This material can then be stored until required to feed the phytoseiid populations.

A considerable advantage of this fast freeze technique is that the bodies of the prey, and more importantly their protein content, will be protected from denaturing.

Using this nutrient material feeding regimes have been established which satisfy the appetites of the predators. Trials have shown that phytoseiid species can, when reared on this new diet, reach the high intrinsic rates of development needed for mass rearing within a commercial enterprise.

The composition of the invention provides a considerable number of advantages over previous combinations. In one aspect the food material used to feed the prey during predator production will no longer be required, therefore providing a substantial cost saving. In another aspect the absence of food materials such as bran will reduce problems of fungal contamination.

The present composition will also eliminate the technical problem of the occurrence of prey imbalance, in which too high or too low prey ratios can cause poor predator development.

Certain predator species seem unable to successfully attack the older stages of the astigmatid hosts, thus restricting their food intake to eggs and larvae. However, it has been observed that when presented with inert bodies feeding activity embraces all stages of the host's life cycle.

In a further advantage the concern that some astigmatid species can cause crop damage by feeding on young tender plants will now no longer apply. Nor will there be a problem where some countries invoke quarantine regulations refusing admission to materials containing certain astigmatid species.

A major advantage afforded by the invention concerns the food industry. Because live food storage mites will no longer be present in the composition, then this material, can be safely applied to the fabric of stores or to parcels such as bulk stored cereals, so that particular phytoseiid predators may now form the basis of new biological control programmes. For example, it is now possible to introduce populations consisting solely of the predator *Amblyseius swirskii* into empty stores as a pre-harvest biological control treatment. This is a novel concept.

In another important embodiment, the invention will open up a new approach to developing successful biological control systems for a variety of cash valuable field crops. Such as avocado, banana, grape, coconut and date palm, all of which at present have problems with controlling pests, (Robinson, 1996: Whiley et al, 2002).

In general, where permanently planted field crops are concerned, available biological control programmes have usually employed the 'classical' approach. This involves the selection of a 'local' predator species which inhabits the local flora and may be associated in some way with the prevailing pest fauna. Or, it involves the introduction of a species collected from a different, but climatically similar, geographic region. Either way, the hope is that the selected predator will become permanently established and act as a biological controlling agent. But failure often ensue, for example, as many as six exotic phytoseiid species have been introduced into Californian avocado orchards with the aim of controlling the avocado brown mite. So far none have become established (Whiley et al 2002).

Another difficulty with the classical approach is that when a pest population begins to increase, the incumbent predator population which has been at a subsistence level, will also begin to increase. But this build-up will invariably lag behind that of the pest, on which of course it is dependent for its food supply. This often means that by the time the predator is in sufficient numbers to act as a controlling influence the pest damage has exceeded the allowable economic damage level.

A good example is that of the ladybird/aphid association. An obvious alternative solution would be to develop some form of mass rearing able to produce large numbers of the predator for use in an inundative release programme.

There are well over 2,000 named species belonging to the family Phytoseiidae from which most of the commercial predators have been taken. But, at present, less than ten of them have been mass reared successfully and sold to the grower.

A reason for this paucity of candidates is that often the combination of a plant dwelling phytoseiid and a factitious stored product host is a new experience for both, frequently leading to incompatibility.

Two factors appear to be operating. Firstly, a live population of astigmatid mites are collectively very active, with fast jerky nervous type movements, which limits the capture success of a predator, which will then be reduced to feeding solely upon eggs and may be small, slow moving larva.

A second factor is that astigmatid species are known to posses pherormonal systems, some of which appear to operate as an alarm or defence mechanism frightening away would be predators. Kuwara (1991) demonstrated the presence of an alarm pheromone in all 11 species of the Astigmata investigated so far.

Together, these factors mean that the food supply will be insufficient, reducing the speed of development of the predator. But a high rate of population increase is essential for a mass rearing operation to be successful.

Since in the composition of the invention the prey is entirely inert, these limiting effects will be eliminated. So, for the first time it introduces the possibility of selecting new, particularly local candidates, from the very large natural pool of phytoseiid predators, with the strong chance that they will react favourably to being mass reared for commercial exploitation.

According to a preferred embodiment of the composition, the predator is selected from the sub-family Amblyseiinae, such as from the genus *Amblyseius*, e.g. *Amblyseius swirskii, Amblyseius cucumeris, Amblyseius largoensis, Amblyseius andersoni*; from the genus *Neoseiulus*, e.g. *Neoseiulus womersleyi, Neoseiulus californicus, Neoseiulus fallacis, Neoseiulus iongispinosus*; the genus *Typhlodromalus*, e.g. *Typhlodromalus lailae, Typhlodromalus limonicus*; the genus *Typhlodromips*, e.g. *Typhlodromips montdorensis*; the genus *Euseius*, e.g. *Euseius ovalis, Euseius scutalis, Euseius tularensis, Euseius hibisci*.

In a further embodiment the preferred phytoseiid is selected from the following group: *Amblyseius swirskii, Amblyseius cucumeris, Amblyseius largoensis, Neoseiulus californicus, Neoseiulus fallacis, Neoseiulus longispinosus, Typhlodromalus lailae, Typhlodromips montdorensis, Eeuseius ovalis, Euseius scutalis, Euseius hibisci*.

It should be understood that in another embodiment of the invention that when necessary the phytoseiid predator may be selected from a species other than those which are especially preferred.

According to a further embodiment of the invention the astigmatid material is preferably selected from members of the family Acaridae, such as from the genus *Acarus*, e.g. *Acarus siro, Acarus farris, Acarus immobilis, Acarus chaetoxysilos*; from the genus *Tyrophagus*, e.g. *Tyrophagus longior, Tyrophagus similis, Tyrophagus putrescentiae*; from the genus *Aleuroglyphus*, e.g. *Aleuroglyphus ovatus*; from the genus *Lardoglyphus*, e.g. *Lardoglyphus konoi*; from the genus *Caloglyphus*, e.g. *Caloglyphus mycophagus*; from the genus *Suidasia*, e.g. *Suidasia nesbitti*; from the genus *Thyreophagus*, e.g. *Thyreophagus entomophagus*; from the family Carpoglyyphidae, such as the genus *Carpoglyphus*, e.g. *Carpoglyphus lactis, Carpoglyphus munroi*; from the family Glycyphagidae, such as the genus *Glycyphagus*, e.g. *Glycyphagus domesticus*; the genus *Lepidoglyphus*, e.g. *Lepidoglyphus destructor*; from the genus *Blomia*, e.g. *Blomia freemani*; from the family Chortoglyphydae, such as the genus *Chortoglyphus*, e.g. *Chortoglyphus arcuatus*.

In a further embodiment the invention provides the use of the composition for the control of various insect and mite pests of glasshouse and field crops, including the cosmopolitan western flower thrip, the banana silvering thrip, and a complex of thrip species of avocado: white-fly species, spider mite species, the tomato russet mite, the broad mite, and the avocado brown mite.

Normally a carrier or predator substrate will be present in the mite composition of the invention. Since food material is no longer present, the substrate will be virtually composed of inert vermiculite particles. Thus, it will provide a free flowing material which is advantageous to applications relative to the nature of the crop, crop densities, plant configurations and management practices.

In an additional embodiment quantities of the predator component will be placed in sachets made of a breathable paper which has a small exit hole from which the predators escape on to the crop, together with a small hook by which the sachet can be attached to an individual plant (Sampson, 1998).

In a special embodiment of the invention, it has been established that where the pest situation requires a fast release of predators they can be supplied with just sufficient inert food to encourage a fast exit, known as 'the quick release' system.

Where a slower exit of predators is required, for example, whilst waiting for the pest to arrive in the crop, the inert food material is supplemented with a suitable pollen supply, giving an extended exit time.

Thus, the overall embodiment of the invention provides a method of rearing phytoseiid predators in the absence of a live astigmatid population, giving many advantages, described within the text, which previously have been impossible to achieve.

This invention introduces a new ability to engender the mass rearing of more phytoseiid species, previously not possible. Thus, it is envisaged that for the first time it will be possible to use inundative release programmes of a 'local' or 'exotic' predator not only for protected crops but for use in field situations. Such systems can, for the first time, provide cost effective biological control programmes to protect those organically grown crops which suffer from a low profit margin.

REFERENCES

Cobagnolu, S. 2008. Mites (Acari) associated with stored apricots in Malataya, Elazig and Ismir provinces of Turkey. *Turk entomol*. dk. 32, (1) pp 3-20.

Cunnington, A. M. 1965. Physical limits for complete development of the grain mite, *Acarus siro*, L., (Acarina,: Acaridae) in relation to its world distribution. *J. appl. Ecol.* 2, pp 205-306.

Cunnington, A. M. 1969. Physical limits for the complete development of the copra mite, *Tyrophagus putrescentiae* (Schrank), (Acarina: Acaridae). In *Proc. 2nd Congr. Acarology*, G. O. Evans (Ed) Acad. Kaido Bpest. pp 241-248

Hughes, A. M. 1976. The mites of stored food and houses. Ministry of Agriculture Fisheries and Food. *Technical bulletin* No. 9. Her Majesty's Stationery Office, London. pp 1-400.

Kuwara, Y. 1991. Pheromone studies on astigmatid mites—alarm, aggregation and sex. In *Modern Acarology*, Vol. I, (Eds. F. Dusbabek, and V. Bukvar) pp 43-52. SPB Academic Publishing bv: The Hague and Academia: Prague.

Robinson, J. C. 1996. Bananas and Plantains. *CAB International*, Wallingford. ISBN 0851989853, pp. 238.

Sampson, C. 1998. The commercial development of an *Amblyseius cucumeris* controlled release system for the control of *Frankliniella ocidentalis* in protectted crops. The Brighton Conference—Pests and Diseases, 5B-4, pp. 409-416.

Whiley, A. W. 2002. The Avocado—Botany Production and Uses. *CABI Publishing*, Wallingford. ISBN 0851993575. pp. 416.

The invention claimed is:

1. A method for rearing a phytoseiid predatory mite comprising:
   providing a mite composition comprising:
   a rearing population of a phytoseiid predatory mite species, wherein the phytoseiid predatory species is from the subfamily Amblyseiinae;
   a population of at least one species from the order Astigmata, wherein the at least one species from the order Astigmata is dead before and after being combined with the rearing population of the phytoseiid predatory mite species; and optionally a carrier,
   allowing individuals of the phytoseiid predatory mite to prey on the population of the species from the order Astigmata.

2. The method according to claim 1, wherein the rearing population is maintained at 20-30° C. and 70-90% relative humidity.

3. The method according to claim 2, wherein the relative humidity is 75-85%.

4. The method according to claim 1, further comprising the step of fast freezing the population of the species from the order Astigmata.

5. The method according to claim 1, wherein the phytoseiid predatory species from the subfamily Amblyseiinae is selected from the group consisting of the genus *Amblyseius*, the genus *Neoseiulus*, the genus *Typhlodromalus*, the genus *Typhlodromips*, and the genus *Euseius*.

6. The method according to claim 5, wherein the phytoseiid predatory species is selected from the group consisting of *Amblyseius swirskii, Amblyseius cucumeris, Amblyseius largoensis, Amblyseius andersoni; Neoseiulus womersleyi, Neoseiulus californicus, Neoseiulus fallacis, Neoseiulus longispinosus; Typhlodromalus lailae, Typhlodromalus limonicus; Typhlodromips montdorensis; Euseius ovalis, Euseius scutalis, Euseius tularensis*, and *Euseius hibisci*.

7. The method according to claim 1, further comprising the step of selecting the at least one species from the order Astigmata from the members of the family Acaridae, from the family Carpoglyphidae, from the family Glycyphagidae, and/or from the family Chortoglyphagidae.

8. The method according to claim 7, wherein the at least one species from the order Astigmata is selected from members of the genus *Acarus*, the genus *Tyrophagus*, the genus *Aleuroglyphus*, the genus *Lardoglyphus*, the genus *Caloglyphus*, the genus *Suidasia*, the genus *Thyreophagus*, the genus *Carpoglyphus*, the genus *Glycyphagus*, the genus *Lepidoglyphus*, the genus *Blomia*, and/or the genus *Chortoglyphus*.

9. The method according to claim 7, wherein the at least one species from the order Astigmata is selected from the species: *Acarus siro, Acarus farris, Acarus immobilis, Acarus chaetoxysilos, Tyrophagus longior, Tyrophagus similis, Tyrophagus putrescentiae, Aleuroglyphus ovatus, Lardoglyphus konoi, Caloglyphus mycophagus, Suidasia nesbitti, Thyreophagus entomophagus, Carpoglyphus lactis, Carpoglyphus munroi, Glycyphagus domesticus, Lepidoglyphus destructor, Blomia freemani* and/or *Chortoglyphus arcuatus*.

10. The method according to claim 1, further comprising the step of providing a further nutritional source for the phytoseiid population.

11. The method according to claim 10, wherein the further nutritional source for the phytoseiid population comprises pollen.

12. The method according to claim 1, further comprising reducing or removing the food material used to feed the prey mites.

13. The method according to claim 1, further comprising reducing fungal contamination by exhaustion of the food material for the prey mites.

14. The method according to claim 1, further comprising protecting the protein content of the prey mites from denaturing.

* * * * *